United States Patent [19]

Oaks et al.

[11] Patent Number: 5,050,610
[45] Date of Patent: Sep. 24, 1991

[54] TRANSESOPHAGEAL ULTRASONIC SCANHEAD

[75] Inventors: Frank B. Oaks, Kent; Perry W. Kaminski, Seattle; Eugene A. Larson, Bellevue, all of Wash.

[73] Assignee: Advanced Technology Laboratories, Inc., Bothell, Wash.

[21] Appl. No.: 613,338

[22] Filed: Nov. 14, 1990

[51] Int. Cl.$^5$ .............................................. A61B 8/00
[52] U.S. Cl. .................................. 128/660.01; 128/4; 128/662.03
[58] Field of Search ............. 128/4, 6, 660.01, 660.10, 128/662.06, 662.03

[56] References Cited

U.S. PATENT DOCUMENTS

| | | | |
|---|---|---|---|
| 4,374,525 | 2/1983 | Baba | 128/660.10 |
| 4,407,293 | 10/1983 | Suarez, Jr. et al. | 128/660.01 |
| 4,543,960 | 10/1985 | Harui et al. | 128/662.06 |
| 4,817,616 | 4/1989 | Goldstein | 128/662.06 |
| 4,819,650 | 4/1989 | Goldstein | 128/662.06 |
| 4,924,852 | 5/1990 | Suzuki et al. | 128/4 |
| 4,982,724 | 1/1991 | Saito et al. | 128/4 |

OTHER PUBLICATIONS

"Phased Array Transesophageal Scanhead Operating Instructions" pub. by Advanced Technolgy Laboratories, Inc., 1990.
"Phased Array Transducer Technology for Transesophageal Imaging of the Heart: Current Status and Future Aspects", J. Souquet, (1982).
"Transesophageal Horizontal and Sagittal Imaging of the Heart with a Phased Array System, Initial Clinical Results.", P. Hanrath et al. (1982).

Primary Examiner—Francis Jaworski
Assistant Examiner—George Manuel
Attorney, Agent, or Firm—W. Brinton Yorks, Jr.

[57] ABSTRACT

An ultrasonic transesophageal scanhead is provided which enables a physician to easily and quickly change the orientation of the image plane during a scanning procedure without disrupting control of the scanhead. Means are provided on the external control unit of the scanhead for unambiguously selecting the orientation of the plane which is imaged by the transducers at the end of the probe of the scanhead. In one embodiment of the present invention, a rocker switch is provided on the underside of the control unit, and a lighted indicator is provided on top of the control unit. When the physician desires to change the image plane, the rocker switch is rolled forward to select the transducer elements of the probe which are configured for scanning in the desired image plane. As the rocker switch is moved, the lighted indicator on the top of the control unit provides a visual display pattern aligned either longitudinally or transversely with respect to the axis of the probe. Thus, the physician can change scanning planes without moving his hand from the control unit, and the unit constantly provides an indication of the orientation of the selected plane.

11 Claims, 4 Drawing Sheets

TRANSESOPHAGEAL ULTRASONIC SCANHEAD

This invention relates to ultrasonic diagnostic systems which utilize ultrasonic transducer scanheads to provide diagnostic information concerning a medical patient and, in particular, to scanheads which may be introduced into a body cavity to perform ultrasonic scanning from within the body.

Ultrasonic diagnostic imaging systems are in widespread use for performing ultrasonic imaging and measurements through the use of scanheads which are placed against the skin. Such scanheads are in common use by radiologists, cardiologists, and obstetricians for examinations of the heart, a developing fetus, or internal abdominal organs. These systems operate by controlling the scanhead to transmit ultrasonic energy through the skin and into the body and receiving ultrasonic echoes returned from the internal structure of the body. Such systems are able to noninvasively provide quick and precise diagnosis of various conditions and disease states inside the body.

However, the heart is one organ for which ultrasonic diagnosis has always been difficult. This is because the heart is located in the thoracic cavity, surrounded by the ribs. Ultrasonic scanning through the ribs is not a viable option due to the absorptive and reflective characteristics of bone structure. Accordingly, the accepted clinical procedure is to scan the heart intercostally. But the transmission and reception of ultrasound through the intercostal windows is sometimes not clinically useful, because of acoustic reflections from normal body structures such as the cartilage connected to the ribs.

The advent of endoscopic technology whereby medical devices can be introduced into the body and manipulated external to the body, led to the development of a new technique for ultrasonically scanning the heart: transesophageal echocardiology. By this technique an ultrasonic transducer is located at the end of an elongated probe, which is passed through the patient's mouth and into the esophagus or stomach. From such a position within the thoracic cavity, the ribs no longer pose an impediment to the transmission and reception of ultrasound. The typical transesophageal scanhead includes a control mechanism external to the body, enabling the clinician to manipulate the end of the probe so that the transducer on the probe end is directed as desired toward the heart. This technique, which places the ultrasonic transducer in close proximity to the heart itself, has been found to be most effective in the diagnosis of disease conditions of the heart.

The development of transesophageal echocardiography has resulted in the desire by physicians for two types of images during such a procedure, longitudinal and transverse images. The longitudinal image is a cross-sectional image taken along a longitudinal plane of the heart, and the transverse image is taken along a transverse plane of the heart. Techniques for obtaining these two types of images include the use of two-dimensional arrays of transducer elements which may be electronically selected to form the desired image, and the use of separate transducers, one with a longitudinal orientation and another with a transverse orientation. Through control of the ultrasonic imaging system to which the probe is connected, the clinician can choose one or the other of the two image orientations.

However, it has been found that a physician often needs to change quickly and often from one image orientation to the other. Furthermore, the physician performing the diagnostic procedure usually requires two hands to control the transesophageal probe, one to hold and guide the elongated member, and the other to manipulate the controls which orient the moveable tip of the probe. Accordingly, it is often inconvenient for the physician to change the controls on the imaging system while performing the transesophageal procedure.

In accordance with the principles of the present invention a transesophageal scanhead is provided which enables a physician to easily and quickly change the orientation of the image plane during a scanning procedure without disrupting control of the scanhead. Means are provided on the external control unit of the scanhead for unambiguously selecting the imaging plane. In a preferred embodiment of the present invention, a rocker switch is provided on the underside of the control unit, and a lighted indicator is provided on top of the control unit. When the physician desires to change the image plane, the rocker switch is rolled forward to select the transverse plane and rearward to select the longitudinal plane, in correspondence to the forward and rearward locations of the transducers on the probe tip. As the rocker switch is moved, the lighted indicator on the top of the control unit provides a visual display pattern aligned either longitudinally or transversely with respect to the axis of the probe. Thus, the physician can change scanning planes without moving his hand from the control unit, and the unit constantly provides an indication of the orientation of the selected plane.

Figure 5:
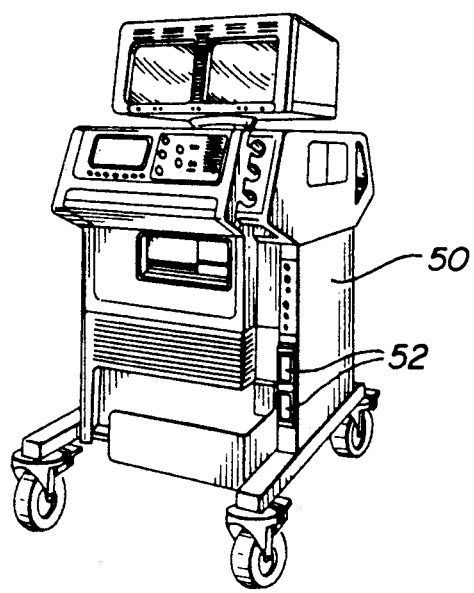
FIGS. 5 and 6 illustrate perspective views of an ultrasonic diagnostic system suitable for use with the scanhead of FIGS. 1-4.
Figure 6:
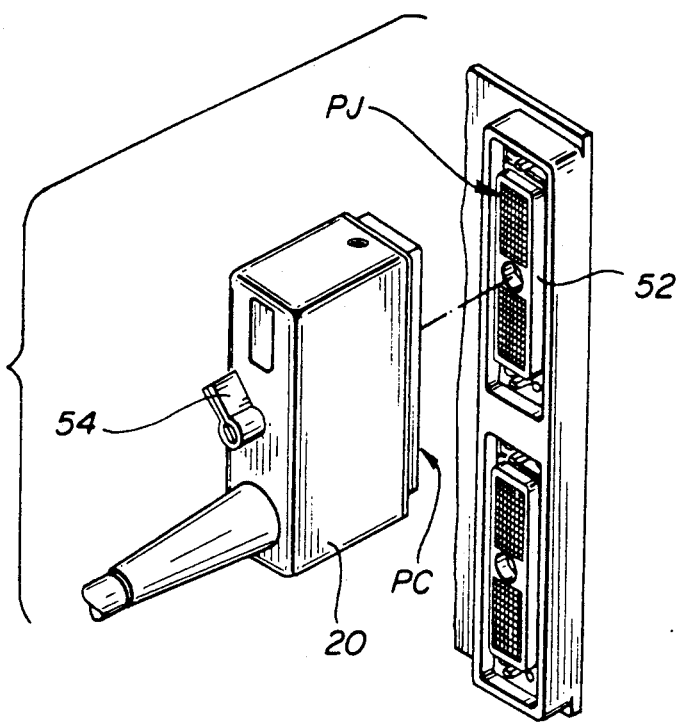
Figure 7B:
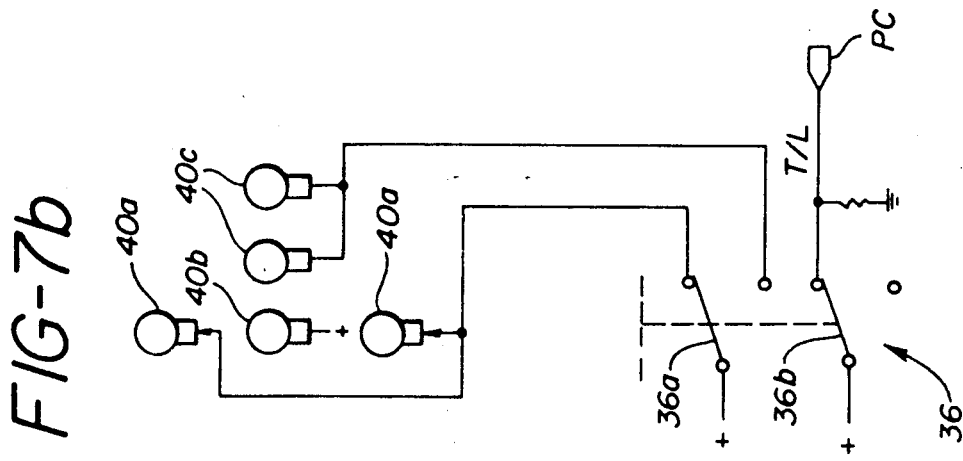
Figure 7A:
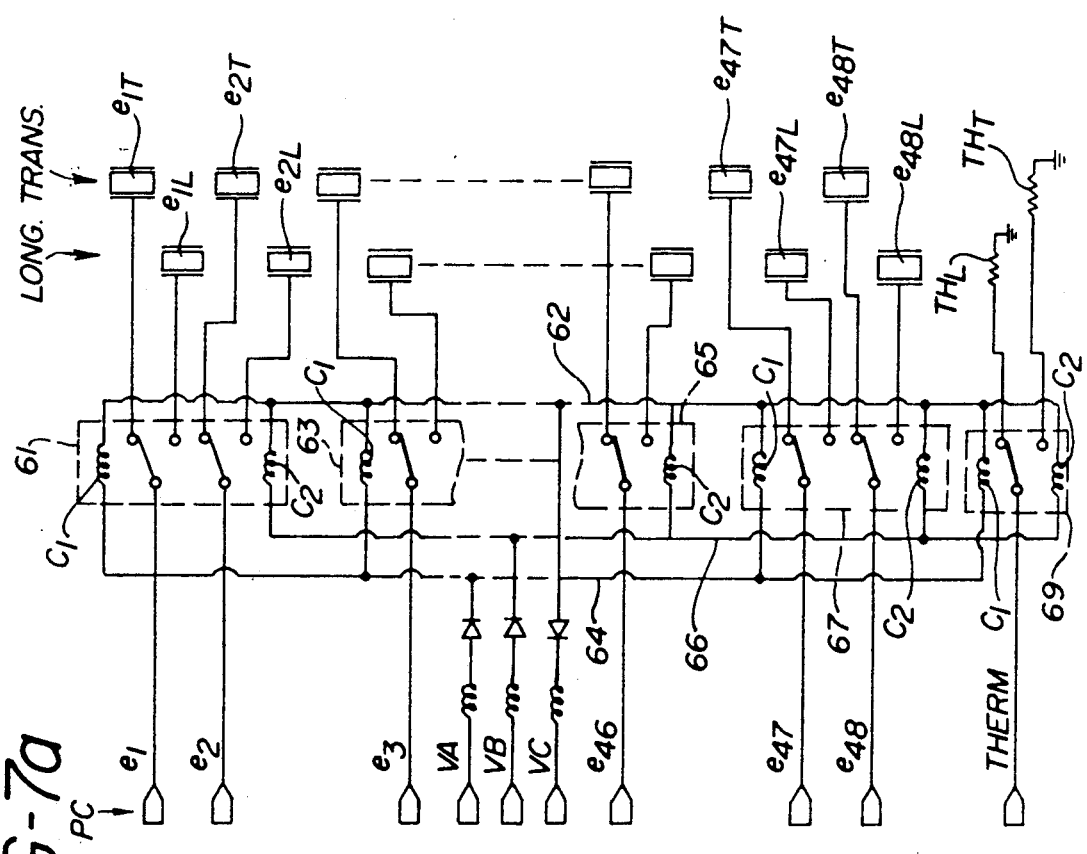
Figure 8:
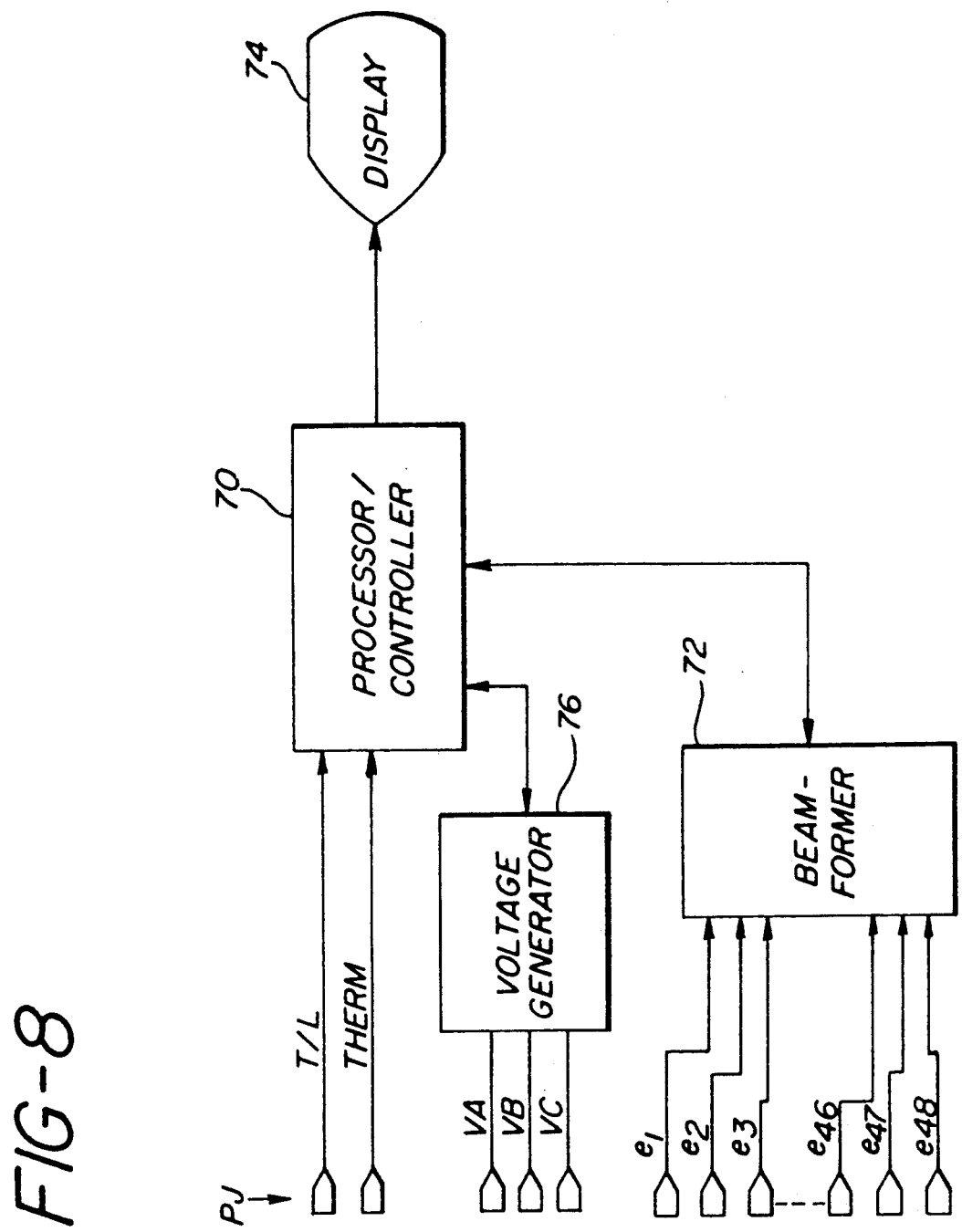

FIGS. 7a and 7b are schematic illustrations of the electronic circuitry of the scanhead of FIGS. 1-4; and FIG. 8 is a block diagram of that portion of the ultrasonic imaging system of FIGS. 5 and 6 which interfaces with the electronic circuitry of FIGS. 7a and 7b.

Figure 1:
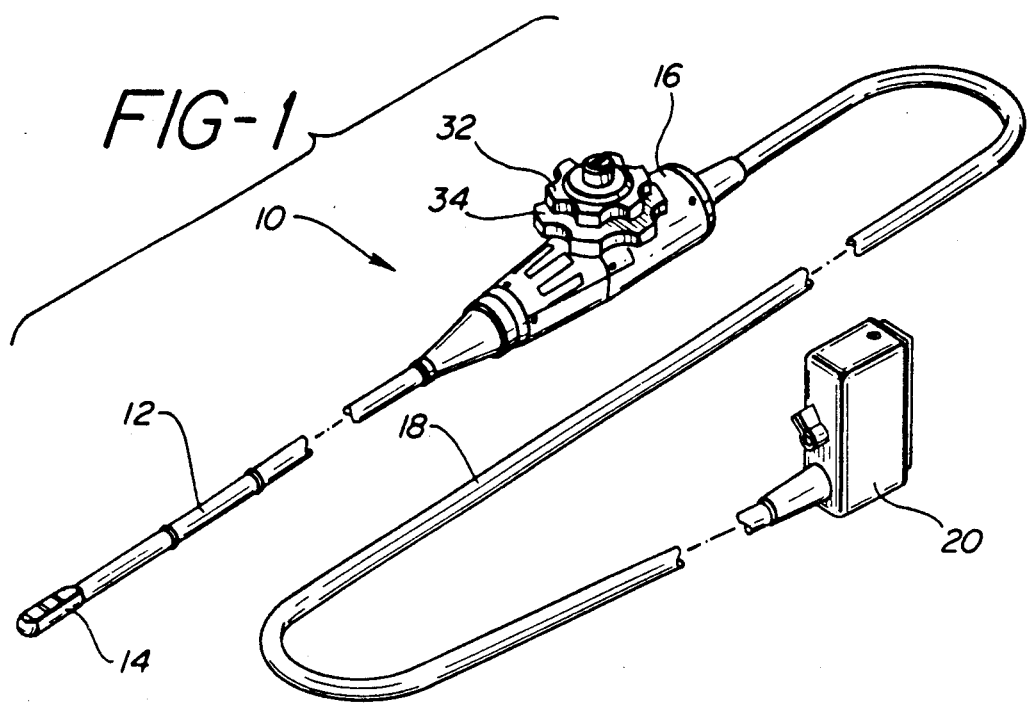
FIG. 1 illustrates a transesophageal scanhead for scanning two orthogonal image planes and constructed in accordance with the principles of the present invention.

Referring first to FIG. 1, a transesophageal scanhead 10 constructed in accordance with the principles of the present invention is shown in perspective. The scanhead includes an elongated tubular probe section 12. The probe section 12 is approximately 100 cm. long and terminates at a distal end 14 on which a pair of ultrasonic transducer arrays are mounted. The probe section 12 contains electrical wires which connect the transducer arrays with a connector 20 at the other end of the scanhead, and stainless steel cables which run to the distal end 14 of the probe and are used to control the orientation of the distal end.

The probe section 12 is connected to the articulating device 16 of the scanhead, which includes two control knobs 32 and 34 for manipulating the distal end of the probe. The control knobs are connected to the cables which extend through the probe section. When knob 32 is turned the distal end 14 of the probe section is moved left and right, and when knob 34 is turned the distal end is moved up and down. The articulating device 16 is connected by a cable 18 enclosing the electrical wiring to a connector 20 which connects the scanhead to an ultrasonic diagnostic system.

Figure 2A:
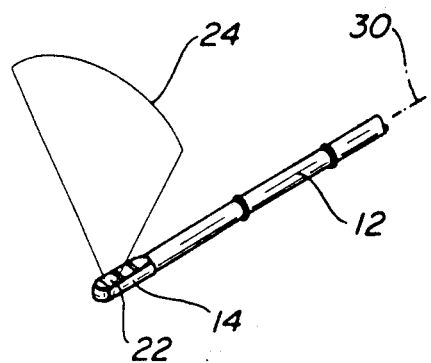
FIGS. 2a and 2b illustrate the image planes scanned by the scanhead of FIG. 1.
Figure 2B:
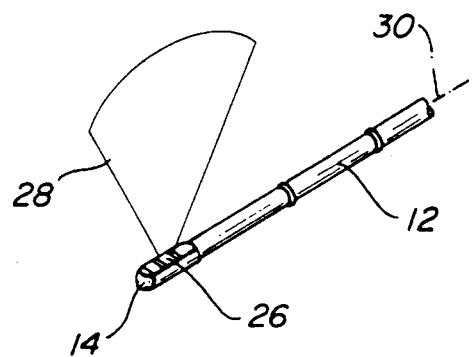

The distal end 14 of the scanhead includes two transducer arrays 22 and 26 which scan the surrounding body during use as shown in FIGS. 2a and 2b. The most distally located transducer array 22 scans a plane 24 of the body which is oriented transversely to the longitudinal axis 30 of the probe section as shown in FIG. 2a. As FIG. 2b shows, when the rearward transducer array 26 is selected, a plane 28 of the body is scanned which is oriented along the longitudinal axis 30 of the probe section. Through selection of the two transducer arrays the clinician is able to scan transverse and longitudinal cross-sectional areas of the heart during use of the scanhead.

Figure 3:
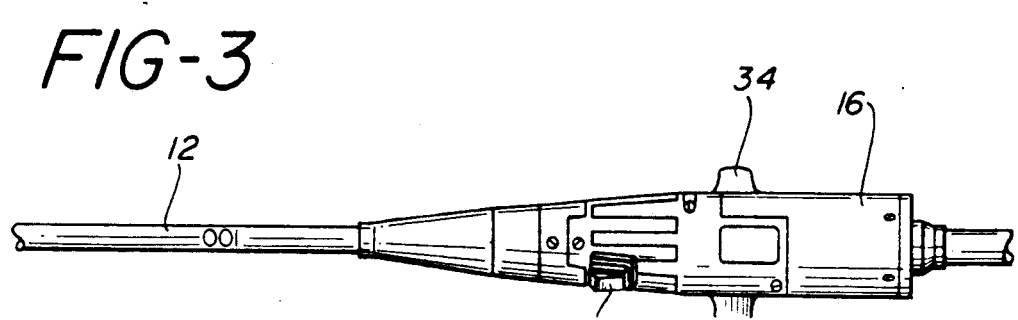
FIG. 3 is a bottom plan view of the control unit of the scanhead of FIG. 1.

FIG. 3 illustrates a bottom plan view of the articulating device 16. Located on the underside of the articulating device is a rocker switch 36. During use of the scanhead at times other than when the distal end of the scanhead is being manipulated, the clinician holds the articulating device with the fingers of a hand cradling the underside of the articulating device. This places the index finger in position to press the rocker switch 36 from one setting to another. As will be described below the scanhead is switched between transverse and longitudinal image planes by pressing the rocker switch 36.

Figure 4:
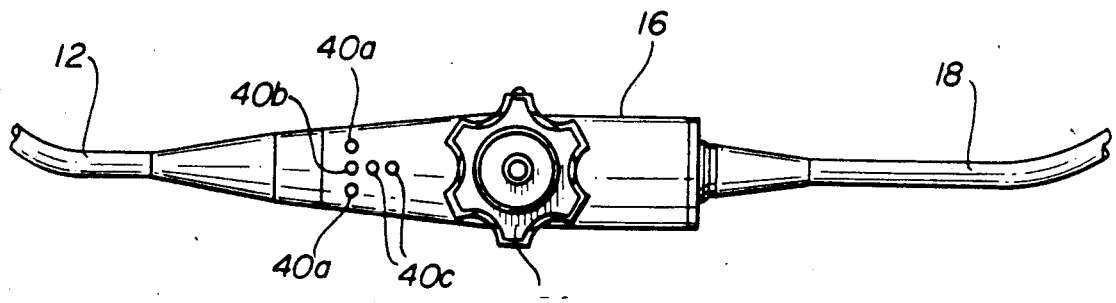
FIG. 4 is a top plan view of the control unit of the scanhead of FIG. 1.

A top plan view of the articulating device 16 is shown in FIG. 4. As this drawing shows, several lights, preferably light emitting diodes (LED's) are located on the upper side of the articulating device 16. Three of the LED's 40a and 40b are arranged in a line transverse to the longitudinal axis of the scanhead, and LED's 40b and 40c are arranged in a line which is parallel to the longitudinal axis. When the articulating device is held by the clinician as described above, appropriate ones of the LED's are illuminated to inform the clinician at a glance as to the orientation of the selected image plane.

FIG. 5 illustrates a perspective view of an ultrasonic diagnostic system 50 suitable for use with a scanhead of the present invention. The diagnostic system 50 includes monitors on top for viewing ultrasonic data and images formed through processing echo information provided by the transesophageal scanhead 10. The connector 20 of the scanhead is plugged into one of the jacks 52 on the front of the system. The system then provides electrical timing and control signals for the scanhead and processes and displays the returning echo information through adjustment of the controls on the front of the system beneath the monitors. FIG. 6 illustrates in detail the connection of the scanhead connector 20 to one of the system jacks 52. The connector is inserted into the jack, aligning pins in the connector (indicated by the arrow PC) with pins in the jack (indicated by arrow PJ). When the key 54 on the connector is turned the pins in the jack and the connector are mated together and the connector is locked in place in the jack.

FIGS. 7a and 7b schematically illustrate the electronic circuitry of the transesophageal scanhead 10 which interacts with the ultrasonic diagnostic system through the connector pins PC. The connector pins PC are shown in the vertical column at the left of FIG. 7a and as shown in FIG. 7b, as well as the signals which are connected by way of the individual pins. In the column labelled "Trans." on the right of the schematic of FIG. 7a are shown specific elements $e_{1T}, e_{2T}, \ldots e_{47T}, e_{48T}$ of the transverse imaging transducer array 22. Adjacent this column of transducer elements is a second column labelled "Long." which indicates individual elements $e_{1L}, e_{2L}, \ldots e_{47L}, e_{48L}$ of the longitudinal imaging transducer array 26. Associated with each transducer array and in contact therewith at the distal end of the scanhead is a thermistor $TH_L$ and $TH_T$, respectively, which senses the temperature of the array during operation. The array elements and thermistors are connected by coaxial wiring extending through the probe section 12, the articulating device 16, and the cable 18 to the remaining electrical components shown schematically in FIG. 7a, which are housed within the connector 20.

The connector 20 physically houses two printed circuit board on which are mounted a number of relays which are controlled by the diagnostic system 50. In a preferred embodiment the printed circuit boards mount twenty-four pulsing relays 61, 63, . . . 65, 67 which are used to connect either the forty-eight elements of the transverse array or the forty-eight elements of the longitudinal array to the diagnostic system 50. An additional pulsing relay 69 switches between the thermistors $TH_L$ and $TH_T$ of the arrays. As FIG. 7a shows, each pulsing relay includes two single pole, double throw switches which are switched in unison under control of relay coils $C_1$ and $C_2$. One side of all of the relay coils is connected to a line 62 and controlled by a signal VC. The other side of relay coils $C_1$ is connected to line 64 and controlled by a signal VA. The other side of relay coils $C_2$ is connected to line 66 and controlled by a signal VB.

FIG. 7b schematically illustrates the electrical connections of the rocker switch 36 and the LED's of the articulating device. The rocker switch 36 includes a double pole, double throw switch mechanism indicated by 36a and 36b. When switch contacts 36a are switched in the illustrated position, LED's 40a are energized by the rocker switch. When the switch contacts 36a are moved to the other switch position, LED's 40c are illuminated. The LED 40b is illuminated whenever the transesophageal scanhead is selected for use by the diagnostic system 50. The other contacts 36b of the switch mechanism apply a positive signal T/L to the diagnostic system 50 when set in the illustrated position, and a low or ground level signal T/L when set in the other position.

FIG. 8 illustrates in block diagram form those portions of the ultrasonic diagnostic system 50 which interact with the signals shown in FIGS. 7a and 7b. To the left of the drawing are shown the pins PJ of the system jack 52. The T/L transducer array selection signal and the thermistor signal THERM are applied to a processor/controller 70. These signals are monitored by the processor/controller to provide indications of the desired image plane of the transesophageal scanhead and any overheating conditions of the transducer array. The processor/controller controls a beamformer 72 to send energizing pulses and receive echo information from the individual transducer elements of the selected transducer array. Received echo information is transferred from the beamformer 72 to the processor/controller 70 for further processing and ultimate display on an image display 74. The processor/controller also controls a voltage generator 76 to send appropriate voltage signals VA, VB, and/or VC to the transesophageal scanhead in response to a change of state of the T/L transducer array selection signal.

Operation of the ultrasonic diagnostic system 50 and the transesophageal scanhead of the present invention may be understood by concurrent reference to FIGS. 7a, 7b, and 8. When the transesophageal scanhead is plugged into the system jack and the scanhead is selected, the system examines the state of the transducer array selection signal T/L. If the rocker switch 36 is set in its forward position, the forwardmost transducer array is selected to image the transverse plane. The switch contacts 36a and 36b are then set as shown in the drawings. Contacts 36a illuminate LED's 40a which, in conjunction with LED 40b, illuminate a transverse pattern across the articulating device. The sensing of a positive T/L signal from the contacts 36b by the processor/controller 70 result in the generation of pulse signals VA and VC. These pulse signals are applied to the pulsing relay coils $C_1$, causing the relays to set in the switch positions shown in FIG. 7a. The pulsing relays thereby connect the forty-eight elements $e_{1T}$-$e_{48T}$ of the transverse imaging array and the its thermistor $TH_T$ to the system beamformer 72. The ultrasonic diagnostic system is now configured to operate the transversely oriented scanhead transducer 22 and display received echo information on the display 74.

If the clinician desires during the diagnostic procedure to switch to the longitudinal scanning mode he merely depresses the rocker switch to the rear. The switch contacts 36a, 36b now are in their alternate positions. Contacts 36a illuminate LED's 40c on the articulating device which, in concert with LED 40b, illuminate a longitudinal pattern along the articulating device. Contacts 36b are now set to apply a ground level T/L signal to the diagnostic system.

The processor/controller responds to the new state of the T/L signal by halting operation of the beamformer 72 for approximately 50 milliseconds. This prevents the transmission of energizing signals to the pulsing relays while the relays are being reset. The processor/controller generates pulse signals VB and VC, which are applied to the pulsing relay coils $C_2$. These pulse signals cause the relays to set in their alternate positions, thereby connecting the elements $e_{1L}$-$e_{48L}$ and thermistor $TH_L$ of the longitudinal array to the beamformer 72. The system and transesophageal scanhead are now configured to scan longitudinal planes using the transducer array 26.

As a further aid to the clinician, the processor/controller may also display a textual message on the image display 74 when the scanning plane is changed. For example, once the image plane has been switched from transverse to longitudinal imaging, the system may display a message such as "LONGITUDINAL IMAGE MODE" for a period of a few seconds. Thus, the selected scanning plane is confirmed visually in two ways to the clinician, periodically on the image display and continuously by the LED display on the transesophageal scanhead itself.

What is claimed is:

1. An ultrasonic diagnostic system, including a scanhead for providing ultrasonic diagnostic information from the interior of a body comprising:
    probe means for insertion into the body, including transducer means having first and second modes of operation for ultrasonic scanning;
    means adapted to be located external to the body during use of the scanhead for manipulating said probe means;
    means for connecting said scanhead to instrument means;
    switch means, located on said manipulating means, for producing a selection signal; and
    means, responsive to said selection signal, for controlling the selection of one of said ultrasonic scanning modes of operation; and
    said system further includes instrument means adapted for coupling with said scanhead connecting means, and responsive to signals by said transducer means for producing a diagnostic image in one or more predetermined image formats, and said instrument means is further responsive to said selection signal for producing a display indicative of said selected mode of operation.

2. The ultrasonic diagnostic scanhead of claim 1, wherein said modes of operation comprise first and second scanning plane orientations relative to said probe means, and wherein said controlling means comprises means for controlling the selection of said scanning plane orientation.

3. The ultrasonic diagnostic scanhead of claim 2, wherein said connecting means includes an output at which ultrasonic information relating to a scanning plane is provided for said instrument means; and said switch means includes a user controlled switch and said controlling means includes electronic switching means responsive to the setting of said switch for selectively coupling ultrasonic information relating to a selected scanning plane between said transducer means and said connecting means output.

4. The ultrasonic diagnostic scanhead of claim 3, wherein said electronic switching means is constructed as a part of said connecting means and is coupled to said connecting means output.

5. The ultrasonic diagnostic scanhead of claim 4, wherein said probe means includes a plurality of transducer elements for scanning in said first and second scanning plane orientations, and wherein said electronic switching means includes a plurality of relays coupled to said transducer elements and said connecting means output.

6. An ultrasonic diagnostic scanhead system for providing ultrasonic diagnostic information from the interior of a body comprising;
    probing means for insertion into the body, including first and second transducer means for scanning in two selectable scanning plane orientations;
    means adapted to be located external to the body during use of the scanhead for manipulating said probe means;
    switch means, located on said manipulating means and producing a control signal, for controlling the selection of said scanning plane orientation;
    means for providing energizing signals for said transducer means;
    means, coupled between said energizing signal providing means and said transducer means, and responsive to the state of said control signal, for selectively applying energizing signals to one of said transducer means, and;
    means for inhibiting said energizing signals while the state of said control signal is changing.

7. The ultrasonic diagnostic scanhead of claim 6, wherein said switch means includes a user controlled switch and wherein said energizing signal applying means includes electronic switching means responsive to the setting of said switch for selectively coupling ultrasonic information relating to a selected scanning plane between said transducer means and a diagnostic instrument.

8. An ultrasonic diagnostic scanhead for providing ultrasonic diagnostic information from the interior of a body comprising:

probe means for insertion into the body, including transducer means for scanning in one of two selectable scanning plane orientations;

means adapted to be located external to the body during use of the scanhead for manipulating said probe means;

means for connecting said scanhead to instrument means for processing electrical information signals produced by said transducer means;

switch means, located on said manipulating means, for controlling the selection of said scanning plane orientation; and display means, coupled to said switch means and located on said manipulating means, for indicating the selected scanning plane orientation.

9. An ultrasonic diagnostic system for providing ultrasonic diagnostic information from the interior of a body comprising:

a scanhead including:

probe means for insertion into the body for scanning in one of two scanning plane orientations relative to said probe means;

means adapted to be located external to the body during use of the scanhead for manipulating said probe means;

means for connecting said scanhead to an operating and control system; and switch means, located on said manipulating means and producing a control signal, for controlling the selection of said scanning plane orientation; and an operating and control system, including means for connecting with said scanhead connecting means;

means for producing an image in a selected scanning plane orientation; and means responsive to the state of said control signal for identifying the selected scanning plane orientation in association with said image.

10. The ultrasonic diagnostic system of claim 9, wherein said operating and control system further includes means responsive to a change of state of said control signal for inhibiting operation of said scanhead for a predetermined time interval.

11. The ultrasonic diagnostic system of claim 9, wherein said probe means includes transducer means for transmitting and/or receiving ultrasonic energy; said scanhead further includes relay means for selectively coupling said transducer means to said scanhead connecting means; and wherein said operating and control system includes means, responsive to the state of said switch means, for energizing said relay means.

* * * * *